under 35 U.S.C. 154(b) by 586 days.

US008232230B2

(12) United States Patent
Volgas et al.

(10) Patent No.: US 8,232,230 B2
(45) Date of Patent: Jul. 31, 2012

(54) MANUFACTURE AND USE OF A HERBICIDE FORMULATION

(75) Inventors: Greg Volgas, Bartlett, TN (US); Johnnie R. Roberts, Memphis, TN (US); Flavious Johnson, Memphis, TN (US)

(73) Assignee: Helena Holding Company, Wilmington, DE (US)

( * ) Notice: Subject to any disclaimer, the term of this patent is extended or adjusted under 35 U.S.C. 154(b) by 586 days.

(21) Appl. No.: 09/916,611

(22) Filed: Jul. 27, 2001

(65) Prior Publication Data

US 2002/0107149 A1     Aug. 8, 2002

Related U.S. Application Data

(60) Provisional application No. 60/250,547, filed on Dec. 1, 2000.

(51) Int. Cl.
*A01N 43/40* (2006.01)
*A01N 43/60* (2006.01)
*A01N 43/42* (2006.01)
*A01N 37/00* (2006.01)
*A01N 37/44* (2006.01)
*A01N 39/02* (2006.01)
*A01N 37/18* (2006.01)

(52) U.S. Cl. ........ 504/130; 504/246; 504/247; 504/254; 504/307; 504/322; 504/323; 504/334

(58) Field of Classification Search .................. 504/145, 504/323, 244, 307; 514/553, 557, 568, 544
See application file for complete search history.

(56) References Cited

U.S. PATENT DOCUMENTS

| | | | |
|---|---|---|---|
| 3,755,339 A | 8/1973 | McKendry | |
| 3,761,486 A | 9/1973 | McGregor | |
| 3,937,826 A | 2/1976 | Harris | |
| 4,445,925 A | 5/1984 | Young | |
| 4,470,840 A | 9/1984 | Welebir | 71/81 |
| 4,767,448 A | 8/1988 | Nielsen | |
| 4,816,060 A | 3/1989 | Steller et al. | |
| 4,863,506 A | 9/1989 | Young | |
| 4,971,630 A | 11/1990 | Skaptason | |
| 4,994,101 A | 2/1991 | Young | |
| 4,995,900 A | 2/1991 | Futcher | 71/92 |
| 5,078,782 A * | 1/1992 | Nielsen et al. | 504/135 |
| 5,096,711 A | 3/1992 | Dookhith et al. | 424/405 |
| 5,118,338 A | 6/1992 | Moller | |
| 5,176,736 A | 1/1993 | Narayanan et al. | |
| 5,178,795 A | 1/1993 | Roberts | 252/356 |
| 5,189,414 A | 2/1993 | Tawara | |
| 5,206,021 A | 4/1993 | Dookhith et al. | 424/405 |
| 5,221,319 A | 6/1993 | Van Haften et al. | |
| 5,234,919 A | 8/1993 | Roberts | 514/119 |
| 5,254,344 A | 10/1993 | Dookhith et al. | 424/405 |
| 5,268,352 A | 12/1993 | Dexter | |
| 5,270,286 A | 12/1993 | Ong | |
| 5,280,008 A | 1/1994 | Cahoy et al. | |
| 5,288,692 A | 2/1994 | Young | |
| 5,317,042 A | 5/1994 | Narayanan | |
| 5,328,889 A | 7/1994 | Van Haften et al. | |
| 5,393,791 A | 2/1995 | Roberts | 514/762 |
| 5,416,067 A | 5/1995 | Van Haften et al. | |
| 5,510,322 A | 4/1996 | Young | |
| 5,558,806 A * | 9/1996 | Policello et al. | 516/204 |
| 5,561,099 A | 10/1996 | Murphy et al. | 504/116 |
| 5,565,409 A | 10/1996 | Sato et al. | |
| 5,580,567 A | 12/1996 | Roberts | 424/405 |
| 5,668,085 A | 9/1997 | Forbes et al. | |
| 5,670,454 A | 9/1997 | Grossmann et al. | 504/244 |
| 5,707,928 A | 1/1998 | Baker | |
| 5,725,630 A | 3/1998 | Roberts et al. | 71/11 |
| 5,741,502 A | 4/1998 | Roberts | 424/405 |
| 5,877,112 A | 3/1999 | Roberts et al. | 504/116 |
| 5,906,961 A | 5/1999 | Roberts et al. | 504/116 |
| 5,994,271 A | 11/1999 | Ravetta et al. | |
| 6,069,115 A | 5/2000 | Pallett et al. | |
| 6,071,857 A | 6/2000 | Vogt et al. | |
| 6,121,200 A * | 9/2000 | Berger et al. | 504/206 |
| 6,165,939 A | 12/2000 | Agbaje et al. | |
| 6,180,563 B1 | 1/2001 | Ruegg et al. | |
| 6,180,566 B1 | 1/2001 | Nielsen et al. | |
| 6,187,715 B1 | 2/2001 | Narayanan et al. | |
| 6,207,617 B1 * | 3/2001 | Gillespie | 504/206 |
| 6,232,272 B1 | 5/2001 | Roberts et al. | 504/323 |
| 6,355,799 B1 | 3/2002 | Gupta et al. | |

(Continued)

FOREIGN PATENT DOCUMENTS

CA       1225533       8/1987

(Continued)

OTHER PUBLICATIONS

Caldwell et al, Toxicity of Herbicides 2,4-D, DEF, propanil, and trifluralin, 1979, Archives of Environmental Contam. and Toxicology, vol. 8 No. 4, pp. 383-396.*
AF 300 from NUFARM, 1999, MSDS, Inosafe No. NU003, AF300 Herbicide.*
WEEDONE® 638 from Rhone-Poulenc Nov. 13, 1998.
ALBAUGH® D-638 from Aulbaugh, Inc. Oct. 2, 1998.
AF 300 from NUFARM (registered 1999) Material Safety Data Sheet, Infosafe No. NU003, AF300 Herbicide.
PCT/US02/08830 International Search Report.
PCT/US02/08787 International Search Report.

(Continued)

*Primary Examiner* — Alton Pryor

(74) *Attorney, Agent, or Firm* — Connolly Bove Lodge & Hutz LLP

(57) ABSTRACT

The invention pertains to a method for manufacture and use of a herbicidal formulation of chlorinated carboxylic acid herbicides. A number of different solvents have been found useful in this application. Furthermore, the use of surfactants that act as solvents for the acid herbicides has been discovered. These formulations have shown superior herbicidal activity when compared to standard salt and ester forms.

68 Claims, No Drawings

U.S. PATENT DOCUMENTS

| | | |
|---|---|---|
| 6,369,001 B1 | 4/2002 | Jimoh |
| 2003/0144147 A1 | 7/2003 | Herold et al. |
| 2003/0148889 A1 | 8/2003 | Herold et al. |

FOREIGN PATENT DOCUMENTS

| | | |
|---|---|---|
| DE | 2328192 | 1/1974 |
| EP | 0100440 | 2/1984 |
| EP | 0163598 | 4/1985 |
| EP | 0216126 | 4/1987 |
| EP | 0217125 | 4/1987 |
| EP | 0243522 | 11/1987 |
| EP | 0334041 | 9/1989 |
| EP | 0357553 | 3/1990 |
| EP | 0 371 212 | 6/1990 |
| EP | 0433577 | 6/1991 |
| EP | 0454968 | 11/1991 |
| EP | 0 554 015 | 8/1993 |
| EP | 0641161 | 10/1996 |
| EP | 0703724 | 2/2002 |
| GB | 2230955 | 11/1990 |
| GB | 2267825 | 12/1993 |
| JP | 58 085805 | 5/1983 |
| RU | 2073974 | 2/1997 |
| WO | WO-92/21686 | 12/1992 |
| WO | WO 94/00986 | 1/1994 |
| WO | WO-94/19941 | 9/1994 |
| WO | WO-96/08150 | 3/1996 |
| WO | WO 97/37978 | 10/1997 |
| WO | WO-98/17109 | 4/1998 |
| WO | WO-99/55155 | 11/1999 |
| WO | WO-00/42847 | 7/2000 |
| WO | WO-00/67571 | 11/2000 |
| WO | WO-01/52650 | 7/2001 |
| WO | WO-02/11536 | 2/2002 |

OTHER PUBLICATIONS

PCT/US02/08952 Annex to Form PCT/ISA/206, Communication Relating to the Results of the Partial Internation Search.
PCT/US02/08953 Annex to Form PCT/ISA/206, Communication Relating to the Results of the Partial Internation Search.
Milton J. Rosen, "Surfactants and Interfacial Phenomena," John Wiley & Sons, pp. 239-240 (1978).
Briggs et al., "Physico-chemical Factors Affecting Uptake by Roots and Translocation to Shoots of Weak Acids in Barley," Pesticide Science, vol. 19, pp. 101-112 (1987).
Wyrill, J.B. et al., "Glyphosate Toxicity to Common Milkweed and Hemp Dogbane as Influenced by Surfactants," Weed Science, vol. 25, No. 3 pp. 275-287 (May 1977).
Tomlin, C., Ed., The Pesticide Manual, Tenth Edition, p. 1338, (1995).
Chemical Abstracts, Turner et al., "Complexing agents as herbicide additives," Weed Res., vol. 18. No. 4, pp. 199-207 (1978).
Chemical Abstracts, McMullan, "Effect of adjuvant and acidifying agent on imazamethabenz efficacy," Can.J.PlantSci., vol. 72, No. 4, pp. 1389-1392 (1992).
Chemical Abstracts, Zsoldos et al., "Effects of ph changes on ion and 2,4-D uptake of wheat roots," Dep. Plant Physiol., pp. 77-80 (1978).
Chemical Abstracts, Shone et al., "Absorption and translocation of 2,4-dichlorophenoxyacetic acid (2,4-D) by barley roots," Annu. Rep.—Agric. Res. Counc., pp. 32-33 (1973).
Chemical Abstracts, Sherrick et al., "Effects of adjuvants and environment during plant development on glyphosate adsorption and translocation in field bindweed," Weed Sci., vol. 34, No. 6, pp. 811-816 (1986).
PCT/US02/08952 International Search Report.
PCT/US02/08953 International Search Report.

* cited by examiner

MANUFACTURE AND USE OF A HERBICIDE FORMULATION

RELATED APPLICATIONS

This application claims benefit to U.S. provisional application Ser. No. 60/250,547 filed Dec. 1, 2000 which is incorporated by reference in its entirety for all useful purposes.

FIELD OF INVENTION

The invention pertains to a method for manufacture and use of a herbicidal formulation of chlorinated carboxylic acid herbicides.

BACKGROUND OF THE INVENTION

Many agricultural formulations contain water-soluble salts of chlorinated carboxylic acid herbicides. These salts, often alkylamine salts or metal salts, are generally not as active as their acid equivalents. For example, (2,4-dichlorophenoxy) acetic acid ("2,4-D") acid is known to be more herbicidally active than the dimethylamine salt of 2,4-D. Also, many of the chlorinated carboxylic acid herbicides are sold to the end users as esters because these esters are more active than the corresponding amine formulation. For instance, it is generally known that 2,4-D ester formulations are more effective as herbicides than 2,4-D amine formulations. The esters, however, are more likely to volatilize even after deposition onto target areas. After volatilization, these esters can cause significant damage to off-target plants.

Chlorinated carboxylic acid herbicides are usually have traditionally been reacted into amine or other salts, which are soluble in water, or into esters which are oil soluble. Both salts and esters must then break down in the environment back into the acid, which is herbicidal.

It would be preferable, then, to apply the herbicides as acids. However, they are not significantly soluble in water. Previously, solvents used to formulate 2,4-D acid such as xylene range hydrocarbons, are known to be phytotoxic to plants and may enhance herbicide volatility and subsequent drift to non-target areas. Albaugh D-638 is one such product, but it further incorporates the ester form of 2,4-D into the formulation. The formulation is 24.5% by weight of 2-butoxyethyl ester of 2,4-dichlorophenoxyacetic acid (CAS #1929-73-3), 13.8% by weight 2,4-D (CAS #94-75-7) and a solvent that contains 7.7% by weight naphthalene (CAS #91-20-3). It is believed that the solvent is Aromatic 150. It is believed that solvent is present in an amount from 55 to 60%. Another commercial product containing the acid form of 2,4-dichlorophenoxyacetic acid is WEEDONE® 638 from Rhone Poulenc (now marketed by Nufarm). This formulation contains 25.2% of the 2-ethylhexyl ester of 2,4-D, 13.8% of the acid form of 2,4-D, 3% propylene glycol, 1.5% titanium oxide and other undisclosed inerts. This formulation is believed to be described in one of the following: U.S. Pat. No. 5,254,344, 5,096,711, or 5,206,021. The 2,4-D in this formulation is not solubolized, but has been dispersed through a water phase.

Another problem associated with the amine salts of some chlorinated carboxylic acid herbicides is their inability to mix with fertilizers. 2,4-D amine herbicides cannot be mixed directly into Uran (urea-ammonia nitrate) fertilizer without some dilution in water. This is a disadvantage for applicators, since this dilution practice increase the total spray volume they must apply per acre.

Surfactants are used in most agricultural formulations to enhance the ease of application. Since many pesticide formulations use hydrophobic solvents, requiring the use of surfactants to emulsify the hydrophobic solvent and pesticide into water. Surfactants have also been used both as adjuvants and formulation components to enhance the effectiveness and spreading ability of applied sprays.

SUMMARY OF THE INVENTION

We have surprisingly discovered that many chlorinated carboxylic acid herbicides can be dissolved into surfactants. These surfactant solubolized herbicides are then seen to have improved spray mix compatibility and improved herbicidal effectiveness. Mixtures of the 2,4-D acid composition and the dicamba formulation produced under this teaching, are fully compatible with Uran fertilizers without any dilution.

One embodiment of the invention is a herbicide composition comprising at least one chlorinated carboxylic acid herbicide and at least one surfactant in an effective amount such that said chlorinated carboxylic acid herbicide is dissolved in the surfactant and said at least one surfactant is present in a quantity equal to or greater than said at least one chlorinated carboxylic acid herbicide.

Another embodiment of the invention is a herbicide composition comprising at least one fully solubolized chlorinated carboxylic acid herbicide and at least about 8 weight % of at least one surfactant.

The invention also related to a process to produce a herbicidal composition which comprises blending a fully solubolized acid herbicide with a surfactant to form a solution provided that said chlorinated carboxylic acid herbicide and surfactant are present in an amount of about 1 part by weight of chlorinated carboxylic acid herbicide to at least about 1.5 part by weight of surfactant.

DETAILED DESCRIPTION OF THE INVENTION

Again, one embodiment of the invention is a herbicide composition comprising at least one chlorinated carboxylic acid herbicide and at least one surfactant in an effective amount such that said chlorinated carboxylic acid herbicide is dissolved in the surfactant and said at least one surfactant is present in a quantity equal to or greater than said at least one chlorinated carboxylic acid herbicide.

Another embodiment of the invention is a herbicide composition comprising at least one fully solubolized chlorinated carboxylic acid herbicide and at least about 8 weight % of at least one surfactant.

The invention also related to a process to produce a herbicidal composition which comprises blending a fully solubolized acid herbicide with a surfactant to form a solution provided that said chlorinated carboxylic acid herbicide and surfactant are present in an amount of about 1 part by weight of chlorinated carboxylic acid herbicide to at least about 1.5 part by weight of surfactant.

Chlorinated carboxylic acid herbicides include, but are not limited to the acid forms of:
- Synthetic auxins including, but not limited to:
  - Benzoic acids such as but not limited to chloramben and dicamba, Phenoxy-carboxylic acids such as but not limited to 2,4,5-trichlorophenoxy acetic acid, 2,4-dichlorophenoxy acetic acid, 2,4-dichlorophenoxy butyric acid, clomeprop, dichlorprop, dichlorprop-P, monochlorophenoxy acetic acid, monochlorophenoxy butyric acid, mecoprop, and mecoprop-P.
  - Pyridine carboxylic acids such as but not limited to clopyralid, fluroxypyr, picloram and triclopyr.

Quinoline carboxylic acids such as but not limited to quinclorac and quinmerac. These herbicides preferably have one of the following 3 general structures Structure 1:

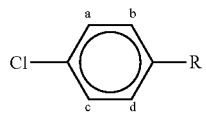

Wherein R is an alkanoic or carboxylic acid group
a, b, c, and d are independently —H, —Cl, —NH$_2$, —CH$_3$, or —OCH$_3$.

Structure 2:

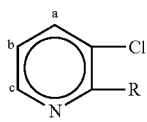

Wherein R is an alkanoic or carboxylic acid group and
a, b and c are independently —H, —Cl, —F, or NH$_2$.

Structure 3:

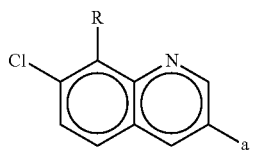

Wherein R is an alkanoic or carboxylic acid group and
a is —Cl, or —CH$_3$
Useful surfactants or solvents include but are not limited to:
Alcohol alkoxylates including but not limited to:
    Based on branched and linear alcohols
    Those containing ethylene oxide or propylene oxide
Alcohol alkoxylate sulfates,
Alkylphenol alkoxylates including but not limited to:
    Nonylphenol and octylphenols.
    Those containing ethylene oxide or propylene oxide
Alkanolamides,
Alkylaryl sulfonates,
Amine oxides
Amines including but not limited to:
Fatty amine alkoxylates such as but not limited to tallowamine alkoxylates,
Betaine derivatives,
Block polymers of ethylene and propylene oxide,
Carboxylated alcohol or alkylphenol alkoxylates,
Diols, including but not limited to Butanediols,
Diphenyl sulfonate derivatives,
Ethers, including but not limited to
    Butyl celluslove,
    Butyl carbitol,
Ethoxylated amines,
Ethoxylated fatty acids,
Ethoxylated fatty esters and oils,
Ethylene carbonate,
Fatty esters,
Glycerol esters,
Glycols including but not limited to
    Propylene glycol,
    Ethylene glycol,
    Dipropylene glycol,
    Diethylene glycol,
Phosphate ester surfactants including but not limited to
    Phosphate esters of alcohol alkoxylates,
    Phosphate esters of alkylphenol alkoxylates,
Propylene Carbonate,
Sarcosine derivatives,
Silicone-based surfactants,
Sorbitan derivatives including but not limited to:
    Sorbitan esters,
    Alkoxylated sorbitan esters,
Sucrose and glucose derivatives including but not limited to:
    Alkylpolyglucosides,
Sulfates and sulfonates of alkoxylated alkylphenols,
Sulfates of alcohols,
Tristyrylphenol Alkoxylates,
Other surfactants are disclosed in McCutcheon's Emulsifiers and Detergents, North American Edition, 2000.
Other surfactants are disclosed in the following patents:
U.S. Pat. No. 5,741,502 Homogeneous, essentially nonaqueous adjuvant compositions with buffering capability
U.S. Pat. No. 5,725,630 Dry granular fertilizer blend and a method of fertilizing plants
U.S. Pat. No. 5,580,567 Homogeneous, essentially nonaqueous adjuvant compositions with buffering capability
U.S. Pat. No. 5,393,791 Homogeneous, essentially nonaqueous adjuvant compositions with buffering capability
U.S. Pat. No. 5,234,919 Water soluble, highly active dimethoate formulations in an alcohol/ester solvent system
U.S. Pat. No. 5,178,795 Homogeneous, essentially nonaqueous adjuvant compositions with buffering capability
U.S. Pat. No. 5,906,961 Alkanolamide spreader-sticker surfactant combination
U.S. Pat. No. 5,877,112 Agricultural formulation
U.S. Pat. No. 6,232,272 Manufacture and use of herbicide chlorinated phenoxy formulation
The formulations may also contain oil-based components.
    The oil or oil substitutes include, but are not limited to:
    Alkylated fatty acid esters, include but are not limited to:
    Methylated fatty acids, include but not limited to:
        Methylated C6-C19 fatty acids,
        Methylated Tall oil fatty acids,
        Methylated Oleic acid,
        Methylated Linoleic acid,
        Methylated Linolenic acid,
        Methylated Stearic acid,
        Methylated Palmitic acid,
        And blends thereof;
    Ethylated fatty acids, include but are not limited to:
        Ethylated C6-C19 fatty acids,
        Ethylated Tall oil fatty acids,
        Ethylated Oleic acid,
        Ethylated Linoleic acid,
        Ethylated Linolenic acid,
        Ethylated Stearic acid,
        Ethylated Palmitic acid,
        And blends thereof;
    Butylated fatty acids, include but are not limited to:
        Butylated C6-C19 fatty acids,
        Butylated Tall oil fatty acids,
        Butylated Oleic acid,
        Butylated Linoleic acid,
        Butylated Linolenic acid, Butylated Stearic acid,
Butylated Palmitic acid,
And blends thereof;
Alkylated natural oils, include but are not limited to:
Alkylated soybean oil, include but limited to:
  Methylated soybean oil,
  Ethylated soybean oil,
  Butylated soybean oil,
  And blends thereof;
Alkylated canola oil, include but are not limited to:
  Methylated canola oil,
  Ethylated canola oil,
  Butylated canola oil,
  And blends thereof;
Alkylated coconut oil, include but are not limited to:
  Methylated coconut oil,
  Ethylated coconut oil,
  Butylated coconut oil,
  And blends thereof;
Alkylated sunflower oil, include but are not limited to:
  Methylated sunflower oil,
  Ethylated sunflower oil,
  Butylated sunflower oil,
  And blend thereof;
Hydrocarbon oils include but are not limited to:
Mineral oils, including but are not limited to:
  Paraffinic mineral oils,
  Naphthenic mineral oils,
  Aromatic mineral oils,
  And blends thereof;
Vegetable oils, include but are not limited to:
Soybean oil,
Canola oil,
Cottonseed oil,
And blends thereof;
Fatty acids, include but are not limited to:
C6-C19 fatty acids,
Tall oil fatty acids,
Oleic acid,
Linoleic acid,
Linolenic acid,
Stearic acid,
Palmitic acid,
And blends thereof;
Polybutenes
Epoxified seed oils include but are not limited to:
  Epoxified soybean oil and
  Other oils or oil substitutes
The formulation can contain at least one of the above oils or its equivalent. The oil can also be a blend of at least two oils. When an oil is used, a surfactant or emulsifier must also be used if the composition is intended for aqueous based sprays. The composition preferably contains (a) from about 1 to about 50% by weight of at least one chlorinated carboxylic acid herbicide, preferably about 5 to about 30% and most preferably about 10 to about 20% and (b) at least about 8% of a surfactant and preferably at least 10% by weight of a surfactant, more preferably at least 20% by weight of a surfactant, more preferably at least 30% by weight of a surfactant and even more preferably from at least 40% by weight of a surfactant and most preferably at least 50% by weight of a surfactant. Again the surfactant can be present in an amount from about 8 to about 99%, preferably about 50 to about 90%, and most preferably about 70 to about 80% and (c) Optionally other components.

The composition can further comprises an ester of (2,4-dichlorophenoxy)acetic acid. The composition according to the invention preferably contains at most 25% by weight of an ester of (2,4-dichlorophenoxy)acetic acid, preferably at most about 15% by weight of an ester of (2,4-dichlorophenoxy) acetic acid, more preferably at most about 10% by weight of an ester of (2,4-dichlorophenoxy)acetic acid, most preferably at most about 5% by weight of an ester of (2,4-dichlorophenoxy)acetic acid and at most about 2% by weight of an ester of (2,4-dichlorophenoxy)acetic acid. Of course, the formulation works with no (2,4-dichlorophenoxy)acetic acid.

The herbicide composition can optionally contain an aromatic solvent. The aromatic solvent is present preferably in an amount of at most 50% by weight and more preferably at most 40% by weight of an aromatic solvent and even more preferably at most 30% by weight of an aromatic solvent and even more preferably at most 20% by weight of an aromatic solvent and even more preferably at most 15% by weight of an aromatic solvent and even more preferably at most 10% by weight of an aromatic solvent and most preferably at most 5% by weight of an aromatic solvent.

The herbicide composition preferably contains a chlorinated carboxylic acid herbicide and a surfactant in the ratio of acid herbicide to surfactant from about 1:6 to about 1:1.

The herbicide composition does not need to contain an alkylated fatty acid, alkylated plant derived oil and/or an alkylated animal derived oil.

Examples of these formulations are shown below:

| Example 1 | |
|---|---|
| 2,4-D Acid Technical | 15.0% |
| $C_{11}$ Alcohol (3EO) Ethoxylate | 85.0% |
| Example 2 | |
| Dicamba acid technical | 15.0% |
| Nonylphenol (6EO) Ethoxylate | 85.0% |
| Example 3 | |
| MCPA acid technical | 10.0% |
| Pluronic L31 | 90.0% |
| Example 4 | |
| 2,4-D acid technical | 20.0% |
| Polyoxyethylene (20) sorbitan monolaurate | 80.0% |
| Example 5 | |
| 2,4-D acid technical | 30.0% |
| Butyl cellusolve | 70.0% |
| Example 6 | |
| 2,4-D acid | 20.0% |
| Methylated soybean oil | 30.0% |
| $C_{11}$ Alcohol (9EO) Ethoxylate | 50.0% |
| Example 7 | |
| 2,4-D Acid technical | 10.0% |
| Dicamba acid technical | 10.0% |
| $C_{11}$ Alcohol (6EO) Ethoxylate Phosphate ester | 80.0% |
| Example 8 | |
| 2,4-D Iso-octyl ester technical | 25.0% |
| Dicamba acid technical | 15.0% |
| $C_{11}$ Alcohol (3EO) Ethoxylate | 60.0% |
| Example 9 | |
| 2,4-D Acid technical | 20.0% |
| Aromatic 150 | 10.0% |
| $C_{11}$ Alcohol (3EO) Ethoxylate | 70.0% |
| Example 10 | |
| 2,4-D P Acid technical | 15.0% |
| $C_{11}$ Alcohol (3EO) Ethoxylate | 85.0% |

-continued

| Example 11 | |
|---|---|
| 2,4-D B acid technical | 15.0% |
| C₁₁ Alcohol (3EO) Ethoxylate | 85.0% |

In all of the above examples, the components are blended together and the technical dissolved entirely. The solution formed contains less than 2% of precipitates and preferably 0% precipitates. Surprisingly, these formulations are compatible with Uran 32 fertilizer.

Various additions can be made to the compositions as one may anticipate based on skill in the art. Other pesticides could be formulated using this composition. Fertilizers could be added to these compositions.

All references discussed herein are incorporated by reference in their entirety for all useful purposes.

We claim:

1. A herbicide composition consisting of components:
(a) at least one chlorinated carboxylic acid herbicide in the acid form wherein said chlorinated carboxylic acid herbicide is Chloramben, dicamba, 2,4,5-trichlorophenoxy acetic acid, 2,4-dichlorophenoxy acetic acid, 2,4-dichlorophenoxy butyric acid, clomeprop, dichlorprop, dichlorprop-P, monochlorophenoxy acetic acid, monochlorophenoxy butyric acid, mecoprop, mecoprop-P.clopyralid, fluoroxypyr, picloram, triclopyr, quinclorac or quinmerac,
(b) at least one surfactant in an effective amount such that said chlorinated carboxylic acid herbicide is fully dissolved in the surfactant and wherein said at least one surfactant is selected from the group consisting of Alcohol alkoxylate,
Alcohol alkoxylate sulfate,
Alkylphenol alkoxylate,
Alkanolamide,
Alkylaryl sulfonate,
Amine oxide,
Betaine,
Block polymers of ethylene and propylene oxide,
Carboxylated alcohol or alkylphenol alkoxylate,
Diphenyl sulfonate,
Ethoxylated amine,
Ethoxylated fatty acid,
Ethoxylated fatty ester and oil,
Ethylene carbonate,
Fatty ester,
Glycerol ester,
Phosphate ester surfactant,
Sarcosine,
Sorbitan,
Sucrose,
Glucose,
Sulfate of alkoxylated alkylphenol,
sulfonate of alkoxylated alkylphenol,
Sulfate of alcohol and
Tristyrylphenol Alkoxylate and optionally
(c) an ester of (2,4-dichlorophenoxy)acetic acid,
and optionally (d) a solvent,
and optionally (e) at least one additional component which is selected from the group consisting of,
Alkylated soybean oil,
Alkylated canola oil,
Alkylated coconut oil,
Alkylated sunflower oil,
Mineral oil,
Vegetable oil,
Fatty acid,
Polybutene and
Epoxified seed oil,
and said at least one surfactant component (b) is present in a quantity equal to or greater than said at least one chlorinated carboxylic acid herbicide component (a).

2. The herbicide composition as claimed in claim 1, wherein at most 25% by weight of the ester of (2,4-dichlorophenoxy)acetic acid is present.

3. The herbicide composition as claimed in claim 1, wherein at most or about 15% by weight of the ester of (2,4-dichlorophenoxy)acetic acid is present.

4. The herbicide composition as claimed in claim 1, wherein at most or about 10% by weight of the ester of (2,4-dichlorophenoxy)acetic acid is present.

5. The herbicide composition as claimed in claim 1, wherein at most or about 5% by weight of the ester of (2,4-dichlorophenoxy)acetic acid is present.

6. The herbicide composition as claimed in claim 1, wherein at most or about 2% by weight of the ester of (2,4-dichlorophenoxy)acetic acid is present.

7. The herbicide composition as claimed in claim 1, wherein said surfactant is present in an amount of at least or about 10% by weight.

8. The herbicide composition as claimed in claim 1, wherein said surfactant is present in an amount of at least or about 20% by weight.

9. The herbicide composition as claimed in claim 2, wherein said surfactant is present in an amount of at least or about 30% by weight.

10. The herbicide composition as claimed in claim 3, wherein said surfactant is present in an amount of at least or about 40% by weight.

11. The herbicide composition as claimed in claim 1, wherein said surfactant is present in an amount of at least or about 50% by weight.

12. The herbicide composition as claimed in claim 2, wherein said surfactant is present in an amount of at least 50% by weight.

13. The herbicide composition as claimed in claim 3, wherein said surfactant is present in an amount of at least 50% by weight.

14. The herbicide composition as claimed in claim 4, wherein said surfactant is present in an amount of at least 50% by weight.

15. The herbicide composition as claimed in claim 5, wherein said surfactant is present in an amount of at least 50% by weight.

16. The herbicide composition as claimed in claim 6, wherein said surfactant is present in an amount of at least 50% by weight.

17. The herbicide composition as claimed in claim 1, wherein said surfactant is present in an amount from about 50 to about 90% by weight.

18. The herbicide composition as claimed in claim 2, wherein said surfactant is present in an amount from about 50 to about 90% by weight.

19. The herbicide composition as claimed in claim 5, wherein said surfactant is present in an amount from about 50 to about 90% by weight.

20. The herbicide composition as claimed in claim 1, wherein said surfactant is present in an amount from about 70 to about 80% by weight.

21. The herbicide composition as claimed in claim 2, wherein said surfactant is present in an amount from about 70 to about 80% by weight.

22. The herbicide composition as claimed in claim 3, wherein said surfactant is present in an amount from about 70 to about 80% by weight.

23. The herbicide composition as claimed in claim 4, wherein said surfactant is present in an amount from about 70 to about 80% by weight.

24. The herbicide composition as claimed in claim 5, wherein said surfactant is present in an amount from about 70 to about 80% by weight.

25. The herbicide composition as claimed in claim 6, wherein said surfactant is present in an amount from about 70 to about 80% by weight.

26. The herbicide composition as claimed in claim 1, wherein said chlorinated carboxylic acid herbicide is present in an amount from about 1 to about 50% by weight.

27. The herbicide composition as claimed in claim 2, wherein said chlorinated carboxylic acid herbicide is present in an amount from about 1 to about 50% by weight.

28. The herbicide composition as claimed in claim 4, wherein said chlorinated carboxylic acid herbicide is present in an amount from about 1 to about 50% by weight.

29. The herbicide composition as claimed in claim 6, wherein said chlorinated carboxylic acid herbicide is present in an amount from about 1 to about 50% by weight.

30. The herbicide composition as claimed in claim 17, wherein said chlorinated carboxylic acid herbicide is present in an amount from about 1 to about 50% by weight.

31. The herbicide composition as claimed in claim 19, wherein said chlorinated carboxylic acid herbicide is present in an amount from about 1 to about 50% by weight.

32. The herbicide composition as claimed in claim 20, wherein said chlorinated carboxylic acid herbicide is present in an amount from about 1 to about 50% by weight.

33. The herbicide composition as claimed in claim 24, wherein said chlorinated carboxylic acid herbicide is present in an amount from about 1 to about 50% by weight.

34. The herbicide composition as claimed in claim 1, wherein said chlorinated carboxylic acid herbicide is present in an amount from about 5 to about 30% by weight.

35. The herbicide composition as claimed in claim 3, wherein said chlorinated carboxylic acid herbicide is present in an amount from about 5 to about 30% by weight.

36. The herbicide composition as claimed in claim 6, wherein said chlorinated carboxylic acid herbicide is present in an amount from about 5 to about 30% by weight.

37. The herbicide composition as claimed in claim 2, wherein said chlorinated carboxylic acid herbicide is present in an amount from about 5 to about 30% by weight.

38. The herbicide composition as claimed in claim 4, wherein said chlorinated carboxylic acid herbicide is present in an amount from about 5 to about 30% by weight.

39. The herbicide composition as claimed in claim 16, wherein said chlorinated carboxylic acid herbicide is present in an amount from about 5 to about 30% by weight.

40. The herbicide composition as claimed in claim 17, wherein said chlorinated carboxylic acid herbicide is present in an amount from about 5 to about 30% by weight.

41. The herbicide composition as claimed in claim 19, wherein said chlorinated carboxylic acid herbicide is present in an amount from about 5 to about 30% by weight.

42. The herbicide composition as claimed in claim 20, wherein said chlorinated carboxylic acid herbicide is present in an amount from about 5 to about 30% by weight.

43. The herbicide composition as claimed in claim 24, wherein said chlorinated carboxylic acid herbicide is present in an amount from about 5 to about 30% by weight.

44. The herbicide composition as claimed in claim 1, wherein said chlorinated carboxylic acid herbicide is present in an amount from about 10 to about 20% by weight.

45. The herbicide composition as claimed in claim 2, wherein said chlorinated carboxylic acid herbicide is present in an amount from about 10 to about 20% by weight.

46. The herbicide composition as claimed in claim 4, wherein said chlorinated carboxylic acid herbicide is present in an amount from about 10 to about 20% by weight.

47. The herbicide composition as claimed in claim 6, wherein said chlorinated carboxylic acid herbicide is present in an amount from about 10 to about 20% by weight.

48. The herbicide composition as claimed in claim 17, wherein said chlorinated carboxylic acid herbicide is present in an amount from about 10 to about 20% by weight.

49. The herbicide composition as claimed in claim 19, wherein said chlorinated carboxylic acid herbicide is present in an amount from about 10 to about 20% by weight.

50. The herbicide composition as claimed in claim 20, wherein said chlorinated carboxylic acid herbicide is present in an amount from about 10 to about 20% by weight.

51. The herbicide composition as claimed in claim 25, wherein said chlorinated carboxylic acid herbicide is present in an amount from about 10 to about 20% by weight.

52. The herbicide composition as claimed in claim 1, wherein an aromatic solvent present in an amount of at most 50% by weight.

53. The herbicide composition as claimed in claim 1, wherein the solvent contains an aromatic solvent present in an amount of at most 40% by weight.

54. The herbicide composition as claimed in claim 1, wherein the solvent contains an aromatic solvent present in an amount of at most 30% by weight.

55. The herbicide composition as claimed in claim 1, wherein the solvent contains an aromatic solvent present in an amount of at most 20% by weight.

56. The herbicide composition as claimed in claim 1, wherein the solvent contains an aromatic solvent present in an amount of at most 15% by weight.

57. The herbicide composition as claimed in claim 1, wherein the solvent contains an aromatic solvent present in an amount of at most 10% by weight.

58. The herbicide composition as claimed in claim 1, wherein the solvent contains an aromatic solvent present in an amount of at most 5% by weight.

59. The herbicide composition as claimed in claim 1, wherein the composition has at most 10% by weight of the ester of (2,4-dichlorophenoxy)acetic acid and said chlorinated carboxylic acid herbicide is present in an amount from about 10 to about 20% by weight, and said surfactant is present in an amount from about 70 to about 80% by weight.

60. The herbicide composition as claimed in claim 59, wherein the solvent is present.

61. The herbicide composition as claimed in claim 1, wherein said at least one additional component is present and is selected from the group consisting of
Methylated C6-C19 fatty acid,
Methylated Tall oil fatty acid,
Methylated Oleic acid,
Methylated Linoleic acid,
Methylated Linolenic acid,
Methylated Stearic acid,
Methylated Palmitic acid,
Ethylated C6-C19 fatty acid,
Ethylated Tall oil fatty acid,
Ethylated Oleic acid,
Ethylated Linoleic acid, Ethylated Linolenic acid,
Ethylated Stearic acid,
Ethylated Palmitic acid,
Butylated C6-C19 fatty acid,
Butylated Tall oil fatty acid,
Butylated Oleic acid,
Butylated Linoleic acid
Butylated Linolenic acid,
Butylated Stearic acid,
Butylated Palmitic acid,
Methylated soybean oil,
Ethylated soybean oil,
Butylated soybean oil,
Methylated canola oil,
Ethylated canola oil,
Butylated canola oil,
Methylated coconut oil,
Ethylated coconut oil,
Butylated coconut oil,
Methylated sunflower oil,
Ethylated sunflower oil,
Butylated sunflower oil,
Paraffinic mineral oil,
Naphthenic mineral oil,
Aromatic mineral oil,
Soybean oil,
Canola oil,
Cottonseed oil,
C6-C19 fatty acid,
Tall oil fatty acid,
Oleic acid,
Linoleic acid,
Linolenic acid,
Stearic acid,
Palmitic acid and
Epoxified soybean oil.

62. The herbicide composition as claimed in claim 2, wherein said at least one additional component is present and is selected from the group consisting of
Methylated fatty acid,
Ethylated fatty acid,
Butylated fatty acid,
Alkylated soybean oil,
Alkylated canola oil,
Alkylated coconut oil,
Alkylated sunflower oil,
Mineral oil,
Vegetable oil,
Fatty acid,
Polybutene and
Epoxified seed oil.

63. The herbicide composition as claimed in claim 2, wherein said at least one additional component is present and is selected from the group consisting of
Methylated C6-C19 fatty acid,
Methylated Tall oil fatty acid,
Methylated Oleic acid,
Methylated Linoleic acid,
Methylated Linolenic acid,
Methylated Stearic acid,
Methylated Palmitic acid,
Ethylated C6-C19 fatty acid,
Ethylated Tall oil fatty acid,
Ethylated Oleic acid,
Ethylated Linoleic acid,
Ethylated Linolenic acid,
Ethylated Stearic acid,
Ethylated Palmitic acid,
Butylated C6-C19 fatty acid,
Butylated Tall oil fatty acid,
Butylated Oleic acid,
Butylated Linoleic acid
Butylated Linolenic acid,
Butylated Stearic acid,
Butylated Palmitic acid,
Methylated soybean oil,
Ethylated soybean oil,
Butylated soybean oil,
Methylated canola oil,
Ethylated canola oil,
Butylated canola oil,
Methylated coconut oil,
Ethylated coconut oil,
Butylated coconut oil,
Methylated sunflower oil,
Ethylated sunflower oil,
Butylated sunflower oil,
Paraffinic mineral oil,
Naphthenic mineral oil,
Aromatic mineral oil,
Soybean oil,
Canola oil,
Cottonseed oil,
C6-C19 fatty acid,
Tall oil fatty acid,
Oleic acid,
Linoleic acid,
Linolenic acid,
Stearic acid,
Palmitic acid and
Epoxified soybean oil.

64. The herbicide composition as claimed in claim 1, wherein the at least one surfactant is selected from the group consisting of
  A) Alcohol alkoxylate based on branched and linear alcohols containing ethylene oxide or propylene oxide
  B) Alcohol alkoxylate sulfate,
  C) Nonylphenol alkoxylate containing ethylene oxide,
  D) Nonylphenol alkoxylate containing propylene oxide,
  E) Octylphenol alkoxylate containing ethylene oxide
  F) Octylphenol alkoxylate containing propylene oxide,
  G) Fatty amine alkoxylate,
  O) Phosphate esters of alcohol alkoxylate,
  P) Phosphate esters of alkylphenol alkoxylate,
  Q) Sorbitan ester,
  R) Alkoxylated sorbitan ester and
  S) Alkylpolyglucoside.

65. The herbicide composition as claimed in claim 2, wherein the at least one surfactant is selected from the group consisting of
  A) Alcohol alkoxylate based on branched and linear alcohols containing ethylene oxide or propylene oxide
  B) Alcohol alkoxylate sulfate,
  C) Nonylphenol alkoxylate containing ethylene oxide,
  D) Nonylphenol alkoxylate containing propylene oxide,
  E) Octylphenol alkoxylate containing ethylene oxide
  F) Octylphenol alkoxylate containing propylene oxide,
  G) Fatty amine alkoxylate,
  O) Phosphate ester of alcohol alkoxylate,
  P) Phosphate ester of alkylphenol alkoxylate,
  Q) Sorbitan ester,
  R) Alkoxylated sorbitan ester and
  S) Alkylpolyglucoside.

66. The herbicide composition as claimed in claim 6, wherein the at least one surfactant is selected from the group consisting of
- A) Alcohol alkoxylate based on branched and linear alcohols containing ethylene oxide or propylene oxide
- B) Alcohol alkoxylate sulfate,
- C) Nonylphenol alkoxylate containing ethylene oxide,
- D) Nonylphenol alkoxylate containing propylene oxide,
- E) Octylphenol alkoxylate containing ethylene oxide
- F) Octylphenol alkoxylate containing propylene oxide,
- G) Fatty amine alkoxylate,
- O) Phosphate ester of alcohol alkoxylate,
- P) Phosphate ester of alkylphenol alkoxylate,
- Q) Sorbitan ester,
- R) Alkoxylated sorbitan ester and
- S) Alkylpolyglucoside.

67. A herbicide composition consisting of components:
- (a) at least one chlorinated carboxylic acid herbicide in the acid form wherein said chlorinated carboxylic acid herbicide is
Chloramben, dicamba, 2,4,5-trichlorophenoxy acetic acid, 2,4-dichlorophenoxy acetic acid, 2,4-dichlorophenoxy butyric acid, clomeprop, dichlorprop, dichlorprop-P, monochlorophenoxy acetic acid, monochlorophenoxy butyric acid, mecoprop, mecoprop-P.clopyralid, fluoroxypyr, picloram, triclopyr, quinclorac or quinmerac,
- (b) at least one surfactant in an effective amount such that said chlorinated carboxylic acid herbicide is fully dissolved in the surfactant and wherein said at least one surfactant is selected from the group consisting of
Alcohol alkoxylate,
Alcohol alkoxylate sulfate,
Alkylphenol alkoxylate,
Alkanolamide,
Alkylaryl sulfonate,
Amine oxide,
Betaine,
Block polymers of ethylene and propylene oxide,
Carboxylated alcohol or alkylphenol alkoxylate,
Diphenyl sulfonate,
Ethoxylated amine,
Ethoxylated fatty acid,
Ethoxylated fatty ester and oil,
Ethylene carbonate,
Fatty ester,
Glycerol ester,
Phosphate ester surfactant,
Sarcosine,
Sorbitan,
Sucrose,
Glucose,
Sulfate of alkoxylated alkylphenol,
sulfonate of alkoxylated alkylphenol,
Sulfate of alcohol and
Tristyrylphenol Alkoxylate and optionally
- (c) an ester of (2,4-dichlorophenoxy)acetic acid, and said at least one surfactant component (b) is present in a quantity equal to or greater than said at least one chlorinated carboxylic acid herbicide component (a).

68. The herbicide composition as claimed in claim 67, wherein said chlorinated carboxylic acid herbicide is present in an amount from about 10 to about 20% by weight and
- at most or about 2% by weight of the ester of (2,4-dichlorophenoxy)acetic acid is present and said surfactant is present in an amount from about 70 to about 80% by weight.

* * * * *